United States Patent [19]
Reed

[11] Patent Number: 4,995,262
[45] Date of Patent: Feb. 26, 1991

[54] TILE SHEAR TESTING APPARATUS AND METHOD

[76] Inventor: Ray M. Reed, 7906 S. Pierce Way, Littleton, Colo. 80123

[21] Appl. No.: 509,019
[22] Filed: Apr. 13, 1990
[51] Int. Cl.$^5$ .............................................. G01N 3/24
[52] U.S. Cl. .................................... 73/842; 73/150 A
[58] Field of Search ................. 73/842, 845, 841, 846, 73/150 A

[56] References Cited

U.S. PATENT DOCUMENTS

| | | | |
|---|---|---|---|
| 2,908,163 | 10/1959 | McClelland | 73/103 |
| 3,566,681 | 3/1971 | Iosipescu et al. | 73/101 |
| 3,911,735 | 10/1975 | Di Crispino | 73/102 |
| 4,343,190 | 8/1982 | Danko et al. | 73/846 |
| 4,346,602 | 8/1982 | Gould et al. | 73/842 |
| 4,823,611 | 4/1989 | Young | 73/842 |

Primary Examiner—Jerry W. Myracle
Attorney, Agent, or Firm—Woodard, Emhardt, Naughton, Moriarty & McNett

[57] ABSTRACT

A tile shear testing apparatus and method is disclosed with a unit having a frame comprising a reaction head and an end plate secured together by a plurality of alignment rods. A movable head is positioned between the end plate and reaction head and is slidable along the alignment rods upon actuation of an expansion unit utilizing fluid pressure. The reaction head and movable head are positioned between two pieces of tile to impart force thereon to determine force necessary to shear the tile-floor bond as measured by a precise digital pressure readout. A swivel jaw engages the tile face and provides pivotable movement to reduce eccentric forces to reduce bending in the frame. Furthermore, the expansion unit's ram piston is positioned low, lying in or near the plane between the tile to reduce eccentric forces tending to bend the frame. The frame is configured to provide ample rigidity.

7 Claims, 6 Drawing Sheets

TILE SHEAR TESTING APPARATUS AND METHOD

BACKGROUND OF THE INVENTION

The present invention relates generally to testing bonding strength between a floor and tiles cemented to the floor, and more specifically is an improvement over the apparatus and method set forth in U.S. Pat. No. 4,823,611 to Young.

It is desirable to test the adhesion strength of cement used to bond tile to an underlying floor. One approach to this problem has been set forth in the aforementioned patent to Young. However, such device in actual usage has shortcomings which can produce inaccurate test results. For example, the Young device tends to pop out of the space between the two tiles being used in the test (reaction tile and test tile) when pressure is applied by the Young device on the tiles. As a result, operators of the Young device sometimes will actually stand on top of the device during operation to prevent it from popping out of the tiles. Such technique significantly distorts the accuracy of the data generated from the Young device.

The present applicant has concluded that two contributing causes to such inaccurate data from the Young device include: (1) force exerted in bending the Young device; and (2) frictional force between the Young device and the floor due especially to the operator standing on the Young device. Each of these problems tend to make the pressure readout on Young artificially higher since the readout actually reflects three forces: the force to bend the Young apparatus frame, frictional forces, and the force to overcome the tile-floor bond. However, with the first two forces not being accounted for, the Young readout tends to inaccurately suggest the tile-floor bond strength is greater than it actually is.

The present invention seeks to overcome these disadvantages of the Young apparatus and method, resulting in more accurate test data. Selected features of the present invention which help overcome these problems include the use of a swivel jaw to engage the face of at least one tile. Accordingly, if the faces of the two tiles to be engaged are not perfectly in alignment, the swivel jaw will compensate, thereby eliminating any eccentric or off-center forces which would tend to bend, twist, and distort the frame. Thus, undue forces are not introduced to bend the frame. Second, a more rigid frame is provided taking into account the cross-sectional moments of inertia along bending axes to provide greater rigidity. With this more rigid frame, less twisting or bending is likely to occur, resulting in more accurate test results. Third, the present invention is arranged so the test apparatus is bridged between the two tiles, rather than resting on the floor, avoiding any frictional forces between the test apparatus and the floor. Fourth, the present invention utilizes a more precise pressure readout with finer increments, allowing for greater precision of data. And fifth, the ram which moves the reaction head and the movable head apart is located on the bottom third of the heads, near the same plane as the tile being tested, to reduce eccentricity and associated bending of the test apparatus frame.

SUMMARY OF THE INVENTION

The present invention provides an apparatus for shear testing bonding strength between a floor and tile cemented to the floor, comprising: a rigid frame including: a reaction head, an alignment end plate, and alignment rods each connecting the reaction head to the alignment end plate; a centrally located movable head in between the reaction head and the alignment end plate, wherein the movable head is slidable along the rods between the reaction head and the alignment end plate in a slide direction generally parallel to the floor; a fluid-pressure activated expansion unit positioned between the reaction head and the centrally located movable head to force the reaction head and the movable head away from one another responsive to increased fluid pressure in the expansion unit, wherein the expansion unit includes a pressure readout; a first jaw attached to the reaction head, the first jaw bearing against a first tile cemented to the floor; and a second jaw attached in a curved notch of the movable head, wherein the second jaw is laterally curved on one face to correspond to the curved notch and is slidable in the curved notch, and wherein the second jaw is generally flat along an opposite face to the curved face to bear against a second tile cemented to the floor, wherein sliding along the curved notch creates a swivel action in the second jaw to engage the second tile flush.

The present invention also provides a method of using the apparatus for testing tile-floor bond strength.

The present invention also provides the inventive apparatus with a ram piston of the expansion unit located along the bottom third of the heads to reduce bending of the frame.

One object of the present invention is to provide an improved tile shear testing apparatus and method.

Another object is to provide more accurate test data for tile-floor bond strength tests.

Another object is to provide a test apparatus which is less likely to bend than prior devices and which involves less frictional losses during testing.

These and other objects are provided in the following specification.

DESCRIPTION OF THE PREFERRED EMBODIMENT

Figure 1:
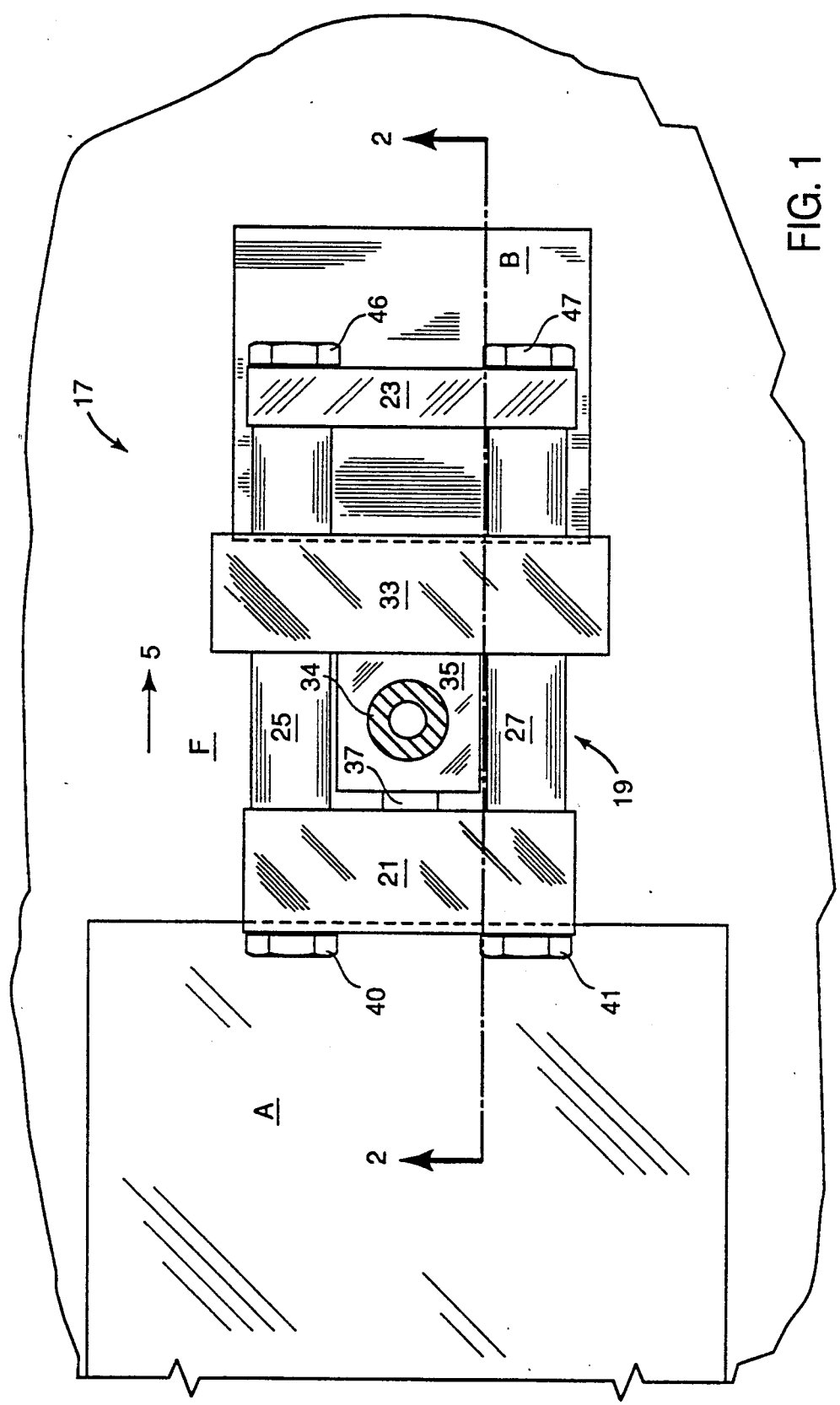
FIG. 1 is a top plan view of the present invention positioned between reaction tile A and test tile B.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device and method, and such further applications of the principles of the invention as illustrated therein being contemplated as would normally occur to one skilled in the art to which the invention relates.

Referring to FIGS. 1-4, a first embodiment of the present inventive shear testing apparatus 17 is illustrated. The testing apparatus includes frame 19, movable head 33 and a fluid-pressure activated expansion unit 35. Frame 19 is rigid and as diagrammed in FIG. 4 includes reaction head 21, alignment end plate 23, alignment rods 25, 27, 29, and 31, and nuts 40, 41, 42, 43 and nuts 46, 47, 48, and 49. A first jaw 51 preferably made of hardened steel is attached to reaction head 21 by screw 67, and a second jaw also made of hardened steel, swivel jaw 53 is attached to movable head 33 by screw 69.

Note that reaction head 21, alignment end plate 23 and movable head 33 are preferably generally rectangular in shape as illustrated, and preferably each lie in planes generally perpendicular to the plane defined by floor F.

Figure 4:
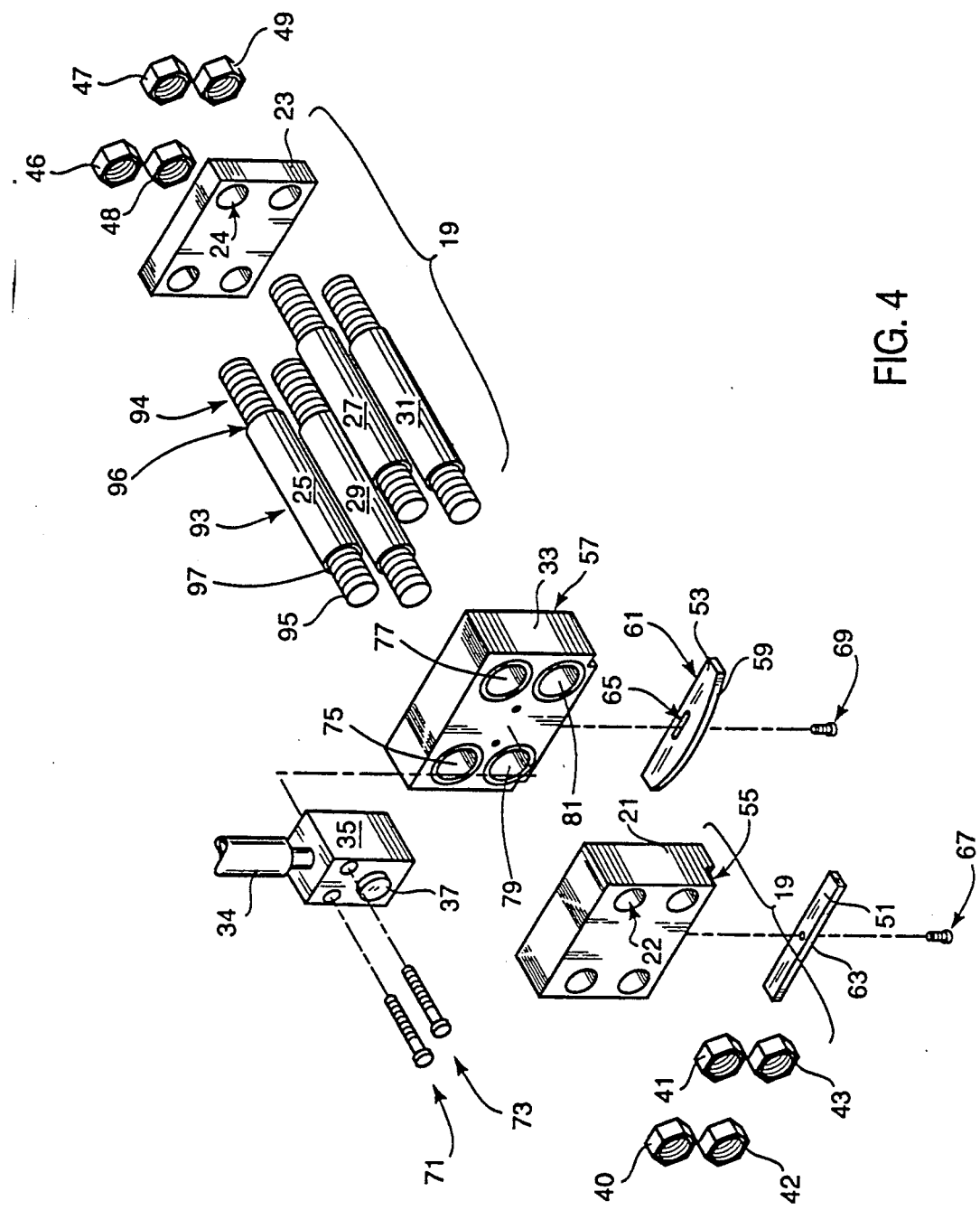
FIG. 4 is an exploded perspective view of the device of FIG. 1.

Referring specifically to FIG. 4, the four alignment rods, 25, 27, 29 and 31 are each respectively disposed in one of four holes, such as hole 24, in alignment end plate 23, and in one of four holes, such as hole 22, in reaction head 21. Furthermore, each of the alignment rods preferably has an enlarged central portion as illustrated, such as enlarged central portion 93 of alignment rod 25. Correspondingly, narrower portions such as narrow front end 94 and narrow rear end 93 are provided forming a front rod shoulder, such as front rod shoulder 96, and a rear rod shoulder, such as rear rod shoulder 97, on each of the alignment rods. Preferably the narrow front end and narrow rear end of the rods are male threaded. In this way, narrow front end 94 is inserted through the hole on plate 23 and receives nut 46, and narrow rear end 95 is disposed through hole liner 75 in movable head 33, and through the hole on reaction head 21 and is male threaded to receive nut 40. The other alignment rods are similarly constructed. The aforementioned shoulders bear against and prevent inward movement of alignment end plate 23 and reaction head 21 respectively. Welding or other securement may be used.

Movable head 33 has holes in it corresponding to the alignment rods with larger diameters to accommodate the enlarged central portions of the alignment rods such as central portion 93. Preferably, the holes in movable head 33 include hole liners, illustrated as hole liner 75, hole liner 77, hole liner 79 and hole liner 81. These hole liners are made up of hardened steel or other such material having a different hardness than the central portion of the alignment rods to eliminate binding and galling on the alignment rods.

Figure 5:
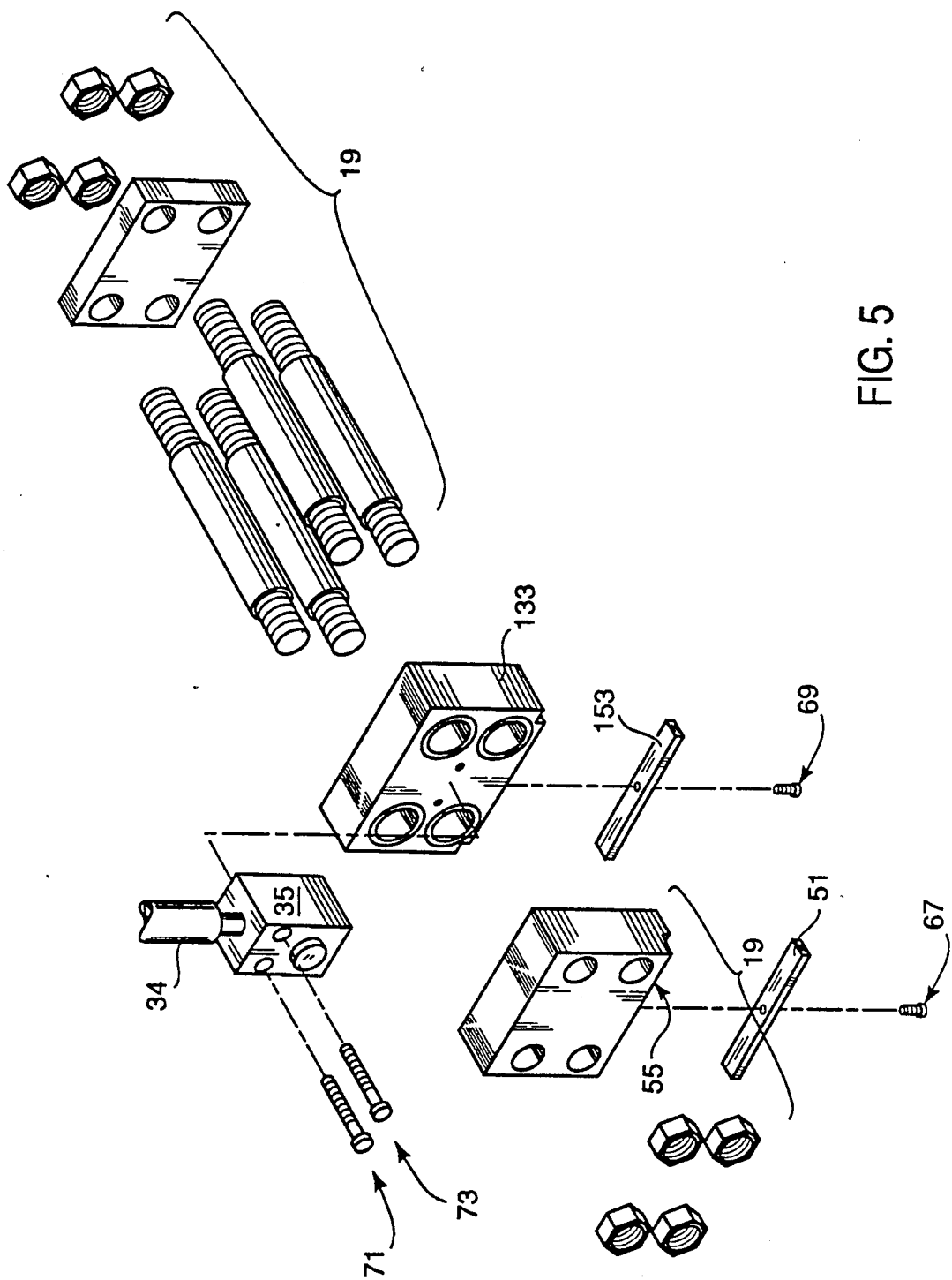
FIG. 5 is an exploded perspective view of a second embodiment of the present invention.

Expansion unit 35 (see FIG. 2) may be purchased off the shelf such as a 5 ton Ram-Pac offered by Duff-Norton of Charlotte, N.C. Expansion unit 35 includes ram piston 37 with a ⅝ inch stroke which is responsive to increased pressure, such as by introducing a fluid like air, oil, or the like. The pressure of the fluid in expansion unit 35 is monitored by a digital pressure readout 38 on pressure gauge 36, preferably having increments with a precision of at least 10 pounds per square inch (or a metric equivalent thereof) and may be incremented down to one pound per square inch as illustrated or less. One example of a pressure gauge which is suitable is a Sensetec, Model No. 060 3155-03 with a zero to 10,000 p.s.i.g. readout, precise to one p.s.i.g. The illustrated readout 38 shows 976 p.s.i.g. Pressurized fluid, such as oil is provided from pump P through hose 39 and hose 34 (shown partially cut) to expansion unit 35, with gauge 36 in-line to monitor pressure (see FIG. 2). Pump P may be a hand operated pump from Hein-Werner, Model No. F.P. 4 for pressures from zero to 10,000 p.s.i.g. As illustrated in FIGS. 4 and 5, expansion unit 35 is mounted to movable head 33 by screw 71 and screw 73. It may be otherwise suitably mounted, for example to reaction head 21 or conceivably left free floating to achieve the purposes of the present invention. Note that unit 35 is arranged so that ram piston 37 is axially centered when viewed from the top (see FIG. 1), and is low, in the bottom third of the height of head 21 and 23 so piston 37 lies near or in the imaginary plane between tile A and tile B. In this way, force by piston 37 is more in alignment with the tile, resulting in less bending in frame 19. This is due to the reduced eccentricity of forces and therefore less bending moment created about bending axis X—X (see FIG. 6) of frame 19.

Jaw 51 is mounted in notch 55 which is lateral with respect to the axial alignment rods and is located on a rear, lower corner of reaction head 21. Similarly, swivel jaw 53 is mounted in notch 57 laterally oriented with respect to the alignment rods and on a front, lower corner of movable head 33. Preferably, notch 57 is laterally curved along a vertical front face and correspondingly, swivel jaw 53 has curved face 59 (see FIGS. 3 and 4). Screw 69 holds jaw 53 and is mounted in lateral slot 65. Accordingly, swivel jaw 53 may swivel with respect to jaw 53 along curved lateral path 83 (see FIG. 3). Front flat face 61 of swivel jaw 53 may engage the vertical face of tile B. flush, reducing any eccentricities which could result if the vertical face of tile B is not perfectly parallel with the vertical face of tile A which is engaged by flat face 63 (see FIG. 4) of jaw 51. In this way, sliding of the swivel jaw along the curved notch creates a swivel action in swivel jaw 53 to engage test tile B flush. It should be appreciated that this swivel action can be achieved by a variety of other structures such as pivots and the like, and furthermore, swivel jaws may be located not only on a movable head as illustrated, but also on the reaction head and/or on both the reaction head and the movable head.

Padding, such as strips of cardboard (not shown) may optionally be used between the jaw faces and the tile to more evenly distribute the force during testing.

Figure 2:
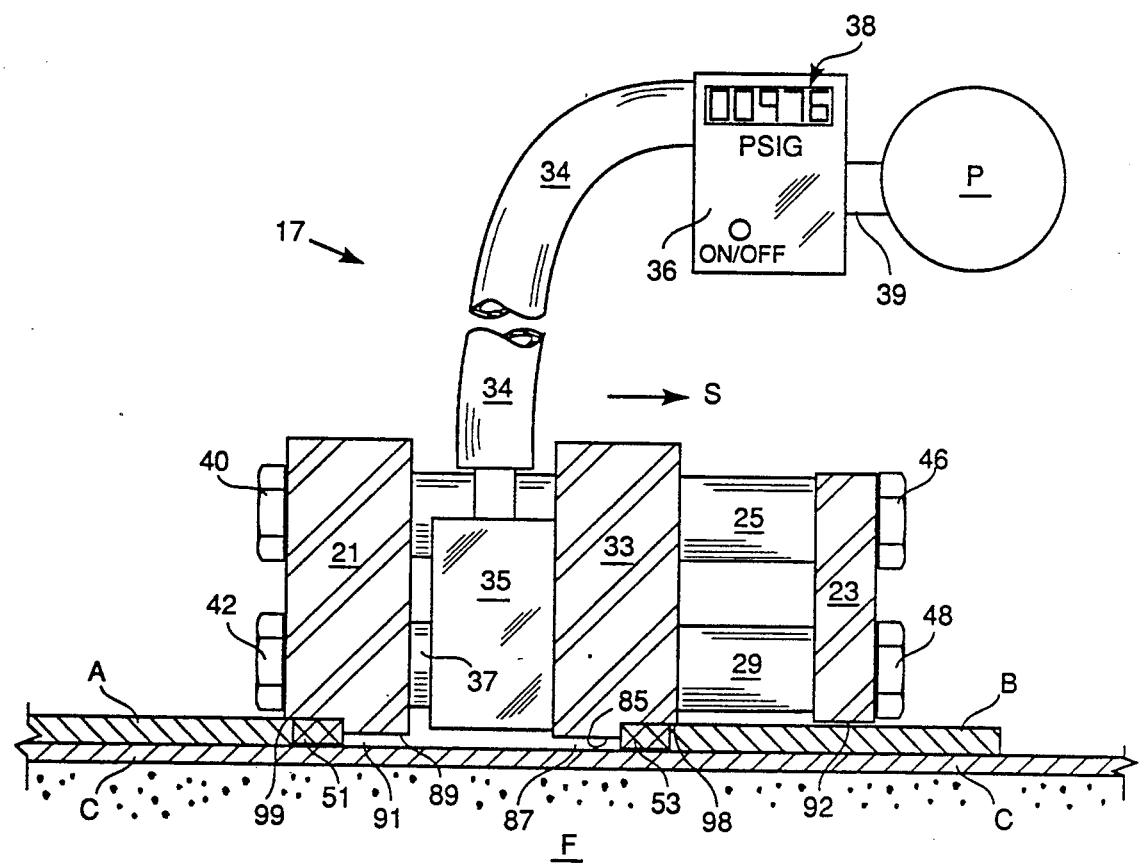
FIG. 2 is a side cross-sectional view of the device of FIG. 1 taken along line 2—2 in FIG. 1.
Figure 3:
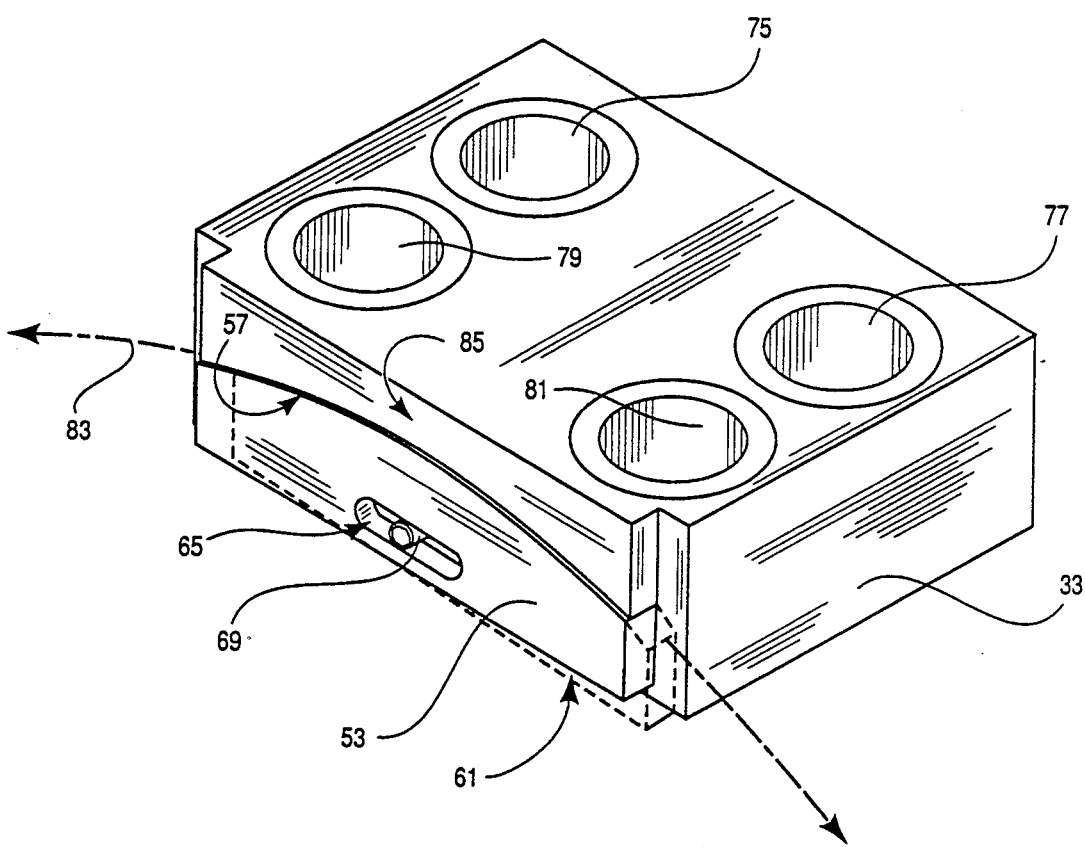
FIG. 3 is a bottom perspective detail view of the movable head utilized in the device of FIG. 1.

Referring specifically to FIG. 2, the present invention is preferably utilized so as to not rest on floor F or the floor's cement C. Gap 87 and gap 91 as illustrated are provided by having the apparatus bridged between reaction tile A and test tile B above and out of contact with floor F and the floor's cement C. Gap 87 is provided by having bottom side 85 of movable head 33 above the cement. Similarly, gap 91 is provided by having bottom side 89 of reaction head 21 above the cement. Bottom side 98 of movable head 33 rests upon test tile B to support the test apparatus 17, and reaction head 21 has bottom side 99 which rests on top of reaction tile A to support apparatus 17. In this way, as described in the background, the apparatus is suspended above the floor, reducing frictional forces (Frictional Force =(coefficient of friction)(normal force)) between the floor and the test apparatus. Similarly, end plate 23 has bottom side 92 which preferably is suspended out of contact with test tile B.

Figure 6:
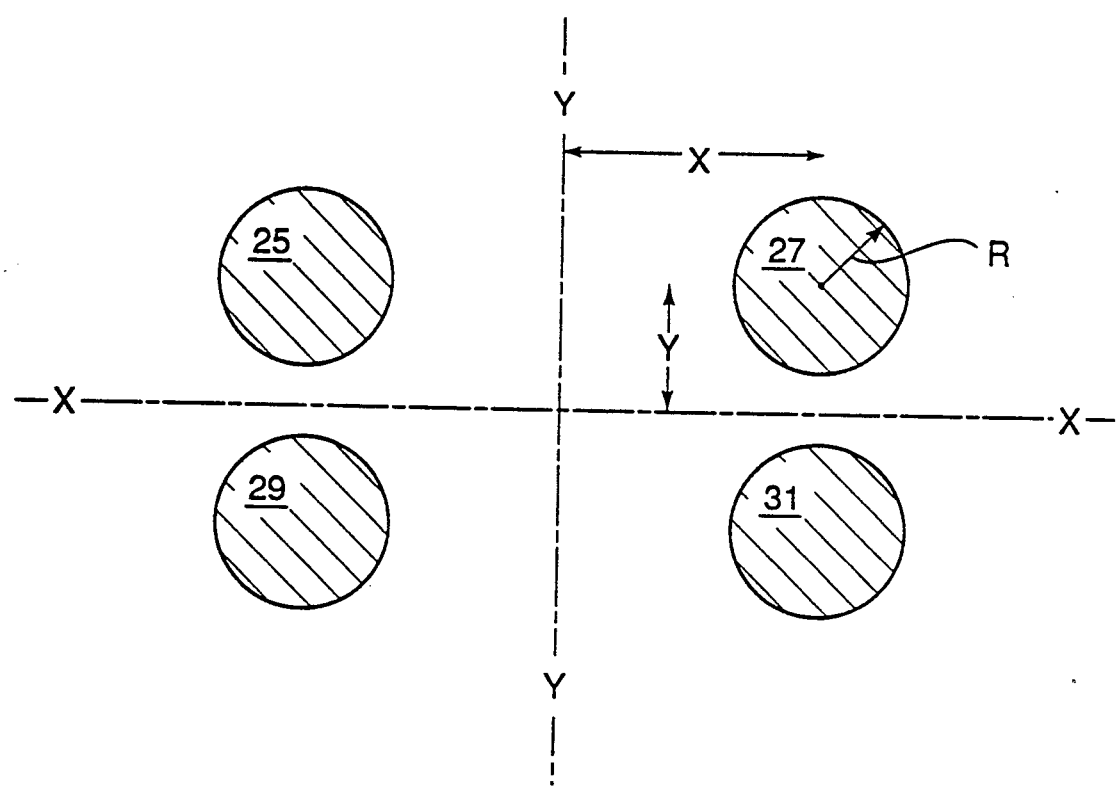
FIG. 6 is a cross-sectional view of the alignment rods of the present invention for purposes of calculating cross-sectional moments of inertia.

Referring particularly to FIG. 6, the cross-sectional moment of inertia of frame 19, and in particular of alignment rods 25, 27, 29 and 31 collectively, may be calculated for bending about the horizontal X—X axis and about the vertical Y—Y axis. In making such calculations, the vertical coordinate Y represents the vertical distance between axis X—X and the centroid of the cross-sectional area of alignment rod 27 taken here as illustrative of the other three alignment rods. Similarly, coordinate X represents the distance between axis Y—Y and the centroid of the area of rod 27. Since rod 27 (and the other alignment rods) are circles, the area thereof is calculated based on radius R of the circle. Calculations are made based on one alignment rod, and since there are four identically situated rods, the result is multiplied by four according to the following equations for determining the moment inertia $I_Y$ about vertical axis Y—Y:

$$I_Y = 4[I_{27} + A_{27}X^2]$$
$$= 4\left[\frac{\Pi R^4}{4} + \Pi R^2 X^2\right]$$

where $I_{27}$ is the moment of inertia for rod 27, and where $A_{27}$ is the area for rod 27.

Similar equations are used for calculation of bending about the X—X axis by substituting the value for the Y coordinate in the equation in place of the X coordinate. For the preferred embodiment, using values of X=1½ inch and R=½ inch, the collective cross-section moment of inertia for the four alignment rods is about 7.25 (in.$^4$). The cross-sectional moment of inertia for bending about the X—X axis with R equal to ½ inch and Y equal to 27/32 of an inch resulting in $I_X$ equal to about 2.43 (in.$^4$). Of course, other configurations may be used, including alignment rods having noncircular cross-sections, greater cross-sectional areas, and other distances for coordinates X and coordinates Y. It is preferred that the moment of inertia about vertical axis Y—Y be at least 5 inches$^4$ and even more, preferably in excess of 7 inches$^4$ to provide rigidity; and that $I_X$ is at least 2 inches$^4$.

Rigidity is also a function of the modulus of elasticity of the material used for alignment rods, and in the present invention they are preferably made of steel and its well known modulus of elasticity of about 29,000 kips per square inch. Another design feature contributing to the rigidity of the present invention is the span length of the alignment rods running between reaction head 21 and plate 23. In the present invention, such span length is about 4⅞ths inches. Furthermore, such span is supported against bending deflection by the presence of movable head 33 located between reaction head 21 and alignment end plate 23. Drawing FIGS. 1 and 2 are proportioned to scale for the preferred embodiment, representing the effective shortened span distances. Thus, the selective placement of the movable head between the end plate and the reaction head provide yet further resistance against deflection and bending.

Referring to FIG. 5, a second embodiment of the present invention is provided. This second embodiment is essentially identical to the embodiment disclosed with regard to FIGS. 1-4 except that swivel jaw 53 is replaced by a nonswiveling jaw 153 which is identical to jaw 51; and, movable head 133 has a lateral notch (not shown) which is not curved, but instead is similar to notch 55.

The method of use of the present invention is discernable from the foregoing written description. As illustrated in FIGS. 1 and 2, apparatus 17 is positioned between tile A and tile B. Tile B comprises a test tile which is separated a distance from reaction tile A. Preferably, reaction tile A is larger than test tile B with a correspondingly greater amount of cement bonding the reaction tile to the floor. In this way, it is the test tile B which is most likely to fail first. Such preparation for testing includes removal of grout as set forth in the Young patent previously discussed, and incorporated herein by reference, and preferably includes sawing test tile B to a standardized size such as 4 inches by 4 inches to allow uniform comparison of test results even when the tile being tested is larger than the standardized test size. After apparatus 17 is positioned, expansion unit 35 is expanded such as by the use of fluid pressure to move ram piston 37, providing a force to move the reaction head and the movable head apart, and correspondingly force jaw 51 and jaw 53 apart. Thus, in operation expansion unit 35 and ram piston 37 cause movable head 33 to move in slide direction S away from reaction head 21. During the application of force, such force is measured on the readout 38 at various stages during an increase of pressure prior to the separation of test tile B from the floor. It is preferred that such readouts be taken with the fluid pressure in unit 35 stabilized to reflect a static test condition rather than testing under dynamic pulsations of fluid pressure as the expansion unit is being pumped up.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An apparatus for shear testing bonding strength between a floor and tile cemented to the floor, comprising:
    (a) a rigid frame including:
        a reaction head being generally rectangular and having at least four holes disposed therein, said reaction head having a lateral notch therein on a rear, lower corner thereof,
        an alignment end plate being generally rectangular and having at least four holes disposed therein, said alignment end plate lying in a plane generally parallel to said reaction head,
        first, second, third, and fourth alignment rods each connecting said reaction head to said alignment end plate and each respectively disposed in one of said four holes in said alignment end plate and one of said four holes in said reaction head, wherein each of said alignment rods has an enlarged central portion along a length thereof and corresponding narrower portions at a front end and a rear end thereof to form a front rod shoulder and a rear rod shoulder on each rod to bear against and prevent inward movement of said alignment end plate and said reaction head respectively, and
        threaded securement members on said front end and said rear end of each of said first, second, third and fourth rods to rigidly secure said rods to said reaction head and to said alignment end plate;
    (b) a centrally located movable head being generally rectangular and having at least four holes disposed therein, said movable head lying in a plane generally parallel to and inbetween said reaction head and said alignment end plate, wherein said four holes in said movable head each have a hardened steel liner disposed therein and disposed around a respective enlarged central portion of a respective one of said first, second, third and fourth alignment rods, wherein said movable head is slidable along said rods between said reaction head and said alignment end plate in a slide direction generally parallel to the floor with said movable head and said reaction head each in a planar orientation generally perpendicular to the floor, wherein said movable head has a laterally curved notch therein on a front, lower corner thereof;

(c) a fluid-pressure activated expansion unit positioned between said reaction head and said centrally located movable head to force said reaction head and said centrally located movable head to force said reaction head and said movable head away from one another responsive to increased fluid pressure in said expansion unit, wherein said expansion unit includes a pressure readout having increments with precision of at least ten pounds per square inch;

(d) a first hardened steel jaw attached in said notch of said reaction head, said first jaw bearing against a first tile cemented to the floor; and (e) a second hardened steel jaw attached in said curved notch of said movable head, wherein said second jaw is laterally curved on one face to correspond to said curved notch and is slidable in said curved notch, and wherein said second jaw is generally flat along an opposite face to said curved face to bear against a second tile cemented to the floor, wherein sliding along said curved notch creates a swivel action in said second jaw to engage said second tile flush.

2. The shear testing apparatus of claim 1 wherein said first and third alignment rods are left side rods, and wherein said second and fourth alignment rods are right side rods, and wherein said left side rods are separated from said right side rods a lateral distance of at least two inches and wherein each of said alignment rods has a diameter of at least one inch, whereby said rigid frame is stiffened against bending about a vertical axis by a cross-sectional moment of inertia of at least seven in.$^4$.

3. The shear testing apparatus of claim 2 wherein said reaction head has a first bottom surface which rests on top of the first tile when said first jaw bears against the first tile, and wherein said movable head has a second bottom surface which rests on top of the second tile when said second jaw bears against the second tile, and wherein said shear testing apparatus is bridged between the first and second tiles above and out of contact with the floor.

4. The shear testing apparatus of claim 3 wherein said expansion unit includes a ram piston positioned to engage said reaction head at a bottom third of said reaction head near a plane between said first and second tile to reduce bending in said frame.

5. The shear testing apparatus of claim 1 wherein said reaction head has a first bottom surface which rests on top of the first tile when said first jaw bears against the first tile, and wherein said movable head has a second bottom surface which rests on top of the second tile when said second jaw bears against the second tile, and wherein said shear testing apparatus is bridged between the first and second tiles above and out of contact with the floor.

6. The shear testing apparatus of claim 1 wherein said expansion unit includes a ram piston positioned to engage said reaction head at a bottom third of said reaction head near a plane between said first and second tile to reduce bending in said frame.

7. A method for shear testing bonding strength between a floor and tile cemented to the floor, comprising:

(1) positioning a testing apparatus between a first tile and a second tile separated a distance from said first tile with both tiles cemented to the floor, said apparatus comprising:

(a) a rigid frame including:

a reaction head being generally rectangular and having at least four holes disposed therein, said reaction head having a lateral notch therein on a rear, lower corner thereof, an alignment end plate being generally rectangular and having at least four holes disposed therein, said alignment end plate lying in a plane generally parallel to said reaction head, first, second, third, and fourth alignment rods each connecting said reaction head to said alignment end plate and each respectively disposed in one of said four holes in said alignment end plate and one of said four holes in said reaction head, wherein each of said alignment rods has an enlarged central portion along a length thereof and corresponding narrower portions at a front end and a rear end thereof to form a front rod shoulder and a rear rod shoulder on each rod to bear against and prevent inward movement of said alignment end plate and said reaction head respectively, and threaded securement members on said front end and said rear end of each of said first, second, third and fourth rods to rigidly secure said rods to said reaction head and to said alignment end plate;

(b) a centrally located movable head being generally rectangular and having at least four holes disposed therein, said movable head lying in a plane generally parallel to and inbetween said reaction head and said alignment end plate, wherein said four holes in said movable head each have a hardened steel liner disposed therein and disposed around a respective enlarged central portion of a respective one of said first, second, third and fourth alignment rods, wherein said movable head is slidable along said rods between said reaction head and said alignment end plate in a slide direction generally parallel to the floor with said movable head and said reaction head each in a planar orientation generally perpendicular to the floor, wherein said movable head has a second lateral notch therein on a front, lower corner thereof;

(c) a fluid-pressure activated expansion unit positioned between said reaction head and said centrally located movable head to force said reaction head and said movable head away from one another responsive to increased fluid pressure in said expansion unit, wherein said expansion unit includes a pressure readout having increments with precision of at least ten pounds per square inch, wherein said expansion unit includes a ram piston positioned to engage said reaction head at a bottom third of said reaction head near a plane between the first and second tile to reduce bending in said frame;

(d) a first hardened steel jaw attached in said notch of said reaction head, said first jaw bearing against the first tile cemented to the floor; and (e) a second hardened steel jaw attached in said notch of said movable head, said second jaw bearing against the second tile cemented to the floor;

(2) expanding said expansion unit with a force wherein said first and second jaws are forced apart; and (3) measuring said force on said readout prior to separation of said second tile from said floor.

* * * * *